United States Patent [19]

O'Brien et al.

[11] Patent Number: 5,246,842
[45] Date of Patent: Sep. 21, 1993

[54] PRODUCTION OF EICOSAPENTAENOIC ACID FROM FILAMENTOUS FUNGI UTILIZING LACTOSE AS A PRIMARY CARBON SOURCE

[75] Inventors: Dennis J. O'Brien, Ambler; Edgar E. Stinson, Melrose Park, both of Pa.; Eric W. Wessinger, Decatur, Ill.; George A. Somkuti, Lansdale, Pa.

[73] Assignee: The United States of America as represented by the Secretary of Agriculture, Washington, D.C.

[21] Appl. No.: 785,375

[22] Filed: Oct. 30, 1991

[51] Int. Cl.⁵ .......................... C12P 7/64; C12N 1/14; C12N 1/00; A61K 31/20
[52] U.S. Cl. .................................. 435/134; 435/254.1; 514/558
[58] Field of Search ..................... 435/134, 911, 254

[56] References Cited

U.S. PATENT DOCUMENTS 4,857,329  8/1989  Sako et al. ........................ 424/195.1
4,870,011  9/1989  Suzuki et al. ........................ 435/134

OTHER PUBLICATIONS

Folch, J., et al., *J. Biol. Chem.*, 226:497–509 (1988).
Slover, H. T. et al., *JAOCS*, 55:933–937 (1979).

*Primary Examiner*—John W. Rollins
*Attorney, Agent, or Firm*—M. Howard Silverstein; John D. Fado; Joseph A. Lipovsky

[57] ABSTRACT

A process for the production of 5,8,11,14,17-eicosapentaenoic acid from filamentous fungi with lactose as a substrate. Preferred filamentous fungi include *Pythium ultimum, Pythium debaryanum,* Pythium sp, and *Pythium irregulare,* the preferred lactose source being whey.

17 Claims, No Drawings

PRODUCTION OF EICOSAPENTAENOIC ACID FROM FILAMENTOUS FUNGI UTILIZING LACTOSE AS A PRIMARY CARBON SOURCE

FIELD OF THE INVENTION

The present invention relates to the production of 5,8,11,14, 17 - eicosapentaenoic acid by use of filamentous fungi utilizing a lactose-containing component, such as whey, as a primary carbon source.

BACKGROUND OF THE INVENTION

Nutritional research has indicated that the addition of 5,8,11,14,17 - eicosapentaenoic acid (EPA), an omega-3 fatty acid, to the human diet appears to reduce triglyceride levels in the blood. This in turn has the potential of reducing the risk of heart disease and atherosclerosis. EPA is also the precursor of several prostaglandins, which are compounds active in lowering blood pressure and causing constriction of the smooth muscle in the bronchi of the lungs. It has also been suggested that EPA may be effective for preventing thrombosis.

If EPA were incorporated into the human diet on a regular basis, the demand for it would substantially increase. This would in turn create a demand for new sources of EPA. The present commercial sources of EPA are concentrated fish oils. These fish oil concentrates are unattractive because they contain cholesterol and have undesirable tastes and odors. Furthermore, fish oils have the potential for containing high levels of heavy metals and pesticides. Thus, there is a need in the art for more attractive sources of omega-3 fatty acids, such as EPA.

While it is known that fungi such as *Saprolegnia parasitica, Phytophthora infestans,* and Mortierella (spp.), contain EPA bearing lipids, it has heretofore not been known that lactose can be used as an energy source for the production of EPA by filamentous fungi. The preferred lactose containing substrate for use in the present invention is whey or a whey product. This is because approximately 47% of whey production presently goes to waste, thus making it available at relatively low expense. The majority of whey produced by industry is in the form of "sweet whey", a by-product of cheese making which typically contains about 5 wt. % lactose. Spray-dried sweet whey permeate (SWP) contains approximately 80 wt. % lactose. It is produced by separating the lactose fraction from the high molecular weight proteins of sweet whey and spray drying it. SWP is a good substrate constituent for organisms which utilize lactose since it also contains minerals, proteins, and vitamins.

The present invention fulfills a need in the art for an inexpensive source of EPA that is not faced with the deficiencies associated with concentrated fish oils.

SUMMARY OF THE INVENTION

In accordance with the present invention, there is provided a method for producing 5,8,11,14,17 - eicosapentaenoic acid (EPA). This comprises: 1) introducing a fungal growth medium containing lactose as the primary carbon source into a fermenter; 2) introducing into said fermenter an inoculum of an EPA-producing filamentous fungus capable of utilizing lactose for growth; and 3) fermenting said ingredients for an amount of time effective for the production of filamentous fungal mycelia, which mycelia possess EPA-containing lipids. Mycelia are defined herein as being an interwoven mass of discrete fungal hyphae or filaments of fungi.

In a preferred embodiment of the present invention, EPA-containing lipids are extracted from the filamentous fungal mycelia. In another preferred embodiment of the present invention, the lactose component is whey or a whey product. In other preferred embodiments of the present invention, the EPA is further extracted from the lipids. In still another preferred embodiment of the present invention, the whey product utilized is a sweet whey permeate and the fungus utilized is *Pythium irregulare.*

DETAILED DESCRIPTION OF THE INVENTION

The present invention is practiced by propagation of the EPA-producing filamentous fungi on a growth media containing the carbohydrate lactose as the primary carbon source. The media is maintained within a pH range of about 5.5 to about 7.5 with a sugar concentration ranging from about 2 g/l to about 10 g/l. The growth medium further contains about 0.1% to about 1.0% by weight of yeast extract and/or mineral salts and/or amino acid supplements; these serving as sources for nitrogen and optionally phosphate. After inoculation the cultures are incubated aerobically at about 12° C. to about 24° C. for a period ranging from about 48 hours to about 240 hours depending on the choice of fungi. Operation of the process is preferably carried out in a sterile environment.

It has been found by the inventors that lactose can be used as either the primary or sole carbon source for the growth of certain filamentous fungi which produce EPA. While some filamentous fungi are known to produce EPA, it has heretofore not been known that lactose can be used as a substrate for the growth of some such fungal species for such a purpose. The preferred source of lactose for the present invention is whey, which is formed during cheese making. It is a watery liquid which separates from the curd after coagulation. Whey typically contains about 5 wt. % lactose, 1 wt. % protein, with the balance being water, vitamins, and the inorganic matter found in milk. Sweet whey permeate (SWP), is whey which has been processed (ultrafiltered) to remove most of the protein and it typically contains about 5 wt. % lactose and about 0.2 to 0.3 wt. % protein, the balance being the inorganic matter of milk. The preferred form of SWP for the present invention is spray-dried and typically contains about 80 wt. % lactose. SWP is preferred because it is readily available as the result of the ultrafiltration of sweet whey in whey protein concentrate production. Other sources of lactose which can be used in the practice of the present invention include any suitable product with a relatively high concentration of lactose, examples of which include spray dried sweet whey powder, demineralized whey, and lactose powder itself.

Filamentous fungi which are suitable for use in the present invention for the production of EPA are those which can utilize lactose as a carbon source for growth, and which also produce EPA as part of their lipid production. Preferred filamentous fungi include those of the class known as Oomycetes. Members include *Pythium ultimum* (ATCC 11123), *Pythium debaryanum* (ATCC 9998), Pythium sp(ATCC 11270) and *Pythium irregulare* (ATCC 10951) with *Pythium irregulare* (ATCC 10951) being preferred.

Any suitable fermenter can be used in the practice of the present invention. Because filamentous fungi exhibit a strong affinity for adhering to surfaces and for surface colonization, any fermenter designed to take advantage of such properties can be used. The particular type of fermenter used in the practice of the present invention is not critical as long as the fermenter is capable of providing the conditions for filamentous fungi growth. Non-limiting examples of suitable fermenters include submerged culture fermenters, as well as the so-called film reactors. A particularly preferred fermenter is described in co-pending U.S. Patent Application, entitled *Attached Growth Biological Reactor*, to O'Brien et al. This co-pending patent application is incorporated herein by reference. The reactor of this co-pending application is comprised of a rigid cylinder which rotates in a trough of nutrient medium. Filamentous fungal growth occurs on the cylinder after an inoculum of said fungus is introduced either into the culture medium or onto the cylinder. As the fungus grows on the cylinder, it is scraped from the cylinder by a doctoring blade and collected in a collection tray for further processing. The entire apparatus is contained in an airtight vessel.

In general, EPA is produced in accordance with the present invention by introducing a nutrient culture medium which contains, inter alia, a nitrogen source, a lactose component as a primary or sole carbon source, and an inoculum of a filamentous fungus, into a fermenter. It may also be desirable to include a phosphorous source, such as potassium diphosphate, and the like. The filamentous fungi are those which are capable of utilizing lactose as a carbon source for growth and which also produce EPA-containing lipids. The inoculum may be prepared by any suitable means. The preparation of a fungal inoculum is well known in the art. For example, an inoculum may be prepared by incubating the fungus from a growing culture on a agar slant in an appropriate growing medium and macerating the mycelia before use.

The resulting mycelia, which bear EPA-containing lipids, is harvested, or separated from the culture medium, by any suitable means. Suitable means include filtration and centrifugation, both of which will leave a wet cake of fungus bodies. While the wet cake, which typically contains about 50 to 80 wt. % water can be dried, such is not preferred for economic, as well as lipid yield considerations.

After harvesting of the EPA-containing mycelia, lipids containing the EPA are extracted from the fungus cells. Suitable methods will generally include the use of an appropriate solvent under conditions which will prevent oxidation of the unsaturated lipids. A conventional technique for extracting lipids from fungus bodies involves homogenizing the fungus bodies in a solvent mixture of chloroform and methyl alcohol. The extracted lipids can then be separated from the solvent mixture by any appropriate method, such as by distillation or flash evaporation of the solvent. In any extraction method, it will be preferred to comminute the fungus bodies, typically by mechanical action such as by crushing or grinding the fungus bodies in the solvent medium. This will increase the efficiency of extraction. Various types of known extraction apparatuses can be used for the purpose of disintegrating the fungus bodies, including the wet-process pulverizing machines, such as ball mills, frictional disk mills, Henshel mixers, and the like. When a wet cake of fungus bodies is added to the alcoholic medium in the pulverizing apparatus and the machine is operated, the fungus bodies are at least partly destroyed or broken by compressive or frictional mechanical force. It will be noted that the fungus bodies should not be disintegrated to an excessive degree that will result in particles which will be too fine to be easily separated from the solvent mixture.

A suitable method for extracting lipids from fungus bodies is taught in U.S. Pat. No. 4,857,329, which is incorporated herein by reference. This '329 patent teaches the extraction of lipids from cells of Mortierella genus fungi by first grinding the cells in the presence, or absence, of a hot alcoholic solvent, and then extracting the alcohol-treated ground cells with a solvent in a supercritical state, or a mixture of a solvent in a supercritical state with a lower aliphatic alcohol, or a lower aliphatic hydrocarbon. The lower aliphatic alcohol is preferably one having a boiling point of about 40° C. to about 120° C., and is selected from the group consisting of ethanol, propanol, isopropanol, butanol, and isobutanol. The preferred lower aliphatic hydrocarbons include butane, pentane, hexane, heptane, and cyclohexane. Preferred process conditions include temperatures from about 35° C. to 90° C. and pressures from about 200 to 600 kg/cm$^2$.

Another method is taught in U.S. Pat. No. 4,870,011, which is also incorporated herein by reference. The method is comprised of mechanical disintegration in two steps, first with an alcohol/water mixture to give a fraction rich in polar lipids, and then with a hydrocarbon solvent, e.g. hexane, to give a fraction lean in polar lipids. A particularly preferred solvent system is a mixture of hexane and isopropanol at a volume to volume ratio of about 3 to 2.

The amount of solvent used in the present invention should be in the range of about 2 to 7 parts by weight, preferably about 3 to 6 parts by weight per part of fungus bodies on a dry basis. It is preferred that water be present with the solvent during extraction. The amount of water to be used with the solvent should be in the range of about 0.2 to 0.7 parts by weight or, preferably, from 0.3 to 0.6 parts by weight per part by weight of the solvent on a anhydrous basis. Such an amount of water can be supplied separately in a calculated weight when the fungus bodies are completely dry, but the amount of separate addition of water should be reduced when the fungus bodies contain water as is the case when a wet cake of the fungus bodies is used.

After solvent extraction of the lipids, the lipids can be separated from the solvent by any suitable technique. Such techniques will usually take advantage of the boiling point difference between the solvent and the lipid fraction. The separation can be accomplished by flashing the solvent from the lipids in an appropriate separation vessel, or by distillation methods. The solvent can be recycled for further extraction.

As previously mentioned, it is preferred that the extraction be accomplished under conditions which will prevent oxidation of the lipids. This can be accomplished by providing a blanket of an inert gas, such as nitrogen, over the mycelia during the extraction process.

The EPA, which will represent about 10 to 20 wt. % of the lipid fraction, can be purified from said lipid fraction by any suitable technique. Such techniques include molecular distillation, separation by formation of urea inclusion compounds, and supercritical fluid extraction.

Having thus described the invention, the following examples are presented for illustrative purposes only and should not be taken as limiting the invention in any way.

EXAMPLE 1

Mycelia of *Pythium debaryanum* (ATCC 9998) were grown from an inoculum grown in Yeast Maintenance (YM) medium comprised of 3 g/l yeast extract (YE), 3 g/l malt extract (ME), and 5 g/l peptone. The inoculum was macerated for 30 sec at low speed in a Waring-type blender. Two mls of the macerated inoculum were added to 100 ml of growth medium in a 250 ml Erlenmeyer flask. The growth medium was 10 g/l spray-dried sweet whey permeate powder (SWP), 3 g/l YE, and 3 g/l $KH_2PO_4$, at a pH of 6.0. The culture was incubated at 24° C. under orbital shaking at 135 rpm and was harvested at 3 days by filtering.

Mycelia dry weights were determined by filtration through Whatman #1 filters and drying to constant weight at 100° C. Glucose concentrations were obtained via a Yellow Springs Instrument Model 27 glucose analyzer. Lactose analyses were performed by high performance liquid chromatography (HPLC). The HPLC consisted of Spectra Physics HPLC modules. The specific modules were an autosampler SP 8780 XR with a 50 ul sample loop, mobile phase pump and pump control unit SP8700, differential refractometer SP 6040, and strip-chart printer/integrator SP4270. The column was an Aminex ion exclusion column, HPX-87H, $300 \times 7.8$ mm, fitted with a Cation-H guard column, $40 \times 4.6$ mm. The mobile phase was helium-sparged 0.3M $HNO_3$ with a flow rate of 0.3 ml/min. Lactose concentrations were measured by peak area mode. A standard mixture, used for identification purposes, was made from triple deionized water, and anhydrous -lactose.

The fatty acid composition of mycelial lipids was determined on a lyophilized culture sample of mycelia extracted with $CHCl_3:CH_3OH$ (2:1 v/v) via the so-called Folch Method. The Folch Method is well known to those skilled in the art and a detailed description of it can be found in *A Simple Method for the Isolation and Purification of Total Lipids From Animal Tissue*, J. Biol. Chem., 226: 497–509, (1988), by J. Folch et al, which is incorporated herein by reference. In this method, the lipid phase of the extract is evaporated to dryness under a stream of nitrogen and weighed. This resulting lipid concentrate is then dissolved in $CHCl_3$ (approximate concentration of 20 mg/ml). A 1 ml lipid sample is then hydrolysed and methylated as described by Slover and Lanza in *Quantitative Analysis of Food Fatty Acids by Capillary Gas Chromatography*, JAOCS, 55:933–937 (1979), and is also incorporated herein by reference. Heptadecanoic acid was used as the internal standard for GC quantification of EPA.

GC was performed using a Hewlett Packard HP 5890 GC (Avondale, Pa.) equipped with a flame ionization detector (FID), a split/splitless injection system and a Supelcowax 10 capillary column, 30 m length $\times 0.32$ mm I.D., having an 0.25 um film thickness. The column oven was programmed for 180° C. isothermal operation for 16 min followed by 3° C./min temperature program to 240° C. final temperature. The detector and injector temperatures were set at 220° C. and the carrier gas (helium) flow rate was approximately 0.92 ml/min. Operating in the split injection mode, the solvent purge rate was 1.0 ml/min and the split vent purge rate was approximately 136 ml/min. Chromatograms were recorded on an HP 3393 A integrator. Standard mixtures used for identification purposes were PUFAs obtained from Supelco Chromatography Products, and fatty acid and fatty acid methyl esters (FAME) standards obtained from Sigma Chemical Co.

EPA identification was based on GC retention times (Rt). This required further analysis before an organism could be verified as an EPA producer. The verification process included co-chromatography of culture samples and culture samples spiked with standard methyl EPA, and GC/MS. EPA was identified if the standard methyl EPA co-eluted with the material expected to be methyl EPA, and the calculated amount of total methyl EPA in the spiked sample equaled the measured amount; the calculated amount was based on the amount measured in the sample not spiked and the amount added to the spiked sample. EPA production was verified with GC/MS by measuring the molecular weight of the compound identified as EPA. GC/MS was performed using an HP 5992 GC/MS instrument operated without FID. Column and oven conditions were the same as for GC. The transfer line temperature to the mass spectrometer was 240° C. The mass analyzer and ion source temperature was 200° C. The injection port temperature was 250° C.

The biomass yield was 4.2 g/l dry weight and the EPA yield Was 15.3 mg/l.

EXAMPLE 2

An inoculum of *Pythium ultimum* (ATCC 11123) was grown in YM medium and macerated for 30 s at low speed in a Waring-type blender. Two mls of this inoculum were aseptically added to a 250 ml Erlenmeyer flask containing 100 ml of a medium consisting of 10 g/l SWP, 3 g/l YE, 3 g/l ME, 5 g/l peptone, and 3 g/l $KH_2PO_4$; pH of the medium was 6.0. The culture was incubated at 24° C. under orbital shaking at 135 rpm and harvested after 4 days.

Lipids and EPA were analyzed in accordance with procedures set forth in Example 1 above. The biomass yield was 3.2 g dry weight/l and the EPA yield was 22.8 mg/l.

EXAMPLE 3

A fermentation of a SWP medium by *Pythium irregulare* was conducted in a 14L New Brunswick Scientific glass vessel. The vessel's baffles and agitation device were removed so that the only mixing was that provided by aeration. A mechanical foam breaker was employed. The temperature was 22° C. and the pH was manually controlled between 5.65 and 6.60.

Experimental Conditions

Inoculum: 5 250 ml Erlenmeyer flasks, each containing 100 ml of YM broth and inoculated with 1 ml on YM broth which had been vortexed for 30 sec in a corn meal agar slant of *Pythium irregulare* were incubated for 3 days at 24° C. The contents of the flasks were then macerated for 45 sec in a 1L Waring-type blender.

Medium: 13.0 g/l sweet whey permeate spray-dried powder (80 wt. % lactose), 3 g/l glucose, 3 g/l YE.

Lipids and EPA were analyzed in accordance with the procedures set forth in Example 1 above.

Results

The fermentation was conducted for 160 hr. and 13 g/l SWP powder was added at 94 hr.

| | |
|---|---|
| Lactose remaining | 2.75 g/l |
| Biomass yield | 3.29 g dry weight/ |
| EPA yield: | |
| % EPA in fatty acids | 16.5 |
| EPA yield in fermenter | 23.9 mg EPA/l |
| Specific Formation of EPA | 7.0 mg EPA/g dry wt. |

We claim:

1. A process for the production of 5,8,11,14,17-eicosapentaenoic acid from filamentous fungi, which method comprises:
   (a) introducing a nutrient medium effective for the growth of filamentous fungi into a reaction vessel, which medium comprises a nitrogen source and a lactose component as the sole or primary carbon source;
   (b) introducing an inoculum of filamentous fungus into said medium, which filamentous fungus is capable of utilizing lactose for growth and is capable of producing lipids which contain 5,8,11,14,17 eicosapentaenoic acid;
   (c) harvesting the resulting mycelia;
   (d) extracting the lipids from said mycelia by first comminuting said mycelia and subsequently treating the mycelia with a solvent selected from the group consisting of $C_2$-$C_4$ aliphatic alcohols, $C_4$-$C_7$ aliphatic hydrocarbons and mixtures thereof; and
   (e) separating the extracted lipids from the mycelia.

2. The process of claim 1 wherein the lactose component is whey or a whey product.

3. The process of claim 2 wherein the whey product is a dry sweet whey permeate.

4. The process of claim 2 wherein the fungus is selected from the group consisting of *Pythium irregulare, Pythium ultimum* and *Pythium debaryanum*.

5. The process of claim 4 wherein the lactose component is dry sweet whey permeate.

6. The process of claim 5 wherein the nutrient medium also contains a source of phosphorus.

7. The process of claim 1 wherein the filamentous fungus is of the class known as the Oomycetes.

8. The process of claim 1 wherein the comminution is accomplished by a mechanical crushing either alone or in combination with grinding action.

9. The process of claim 8 wherein the solvent is an alcohol.

10. The process of claim 9 wherein the alcohol is ethanol or isopropanol.

11. The process of claim 9 wherein the solvent is a mixture of hexane and isopropanol.

12. The process of claim 1 wherein the lipids are extracted from the mycelia with the solvent in the presence of water.

13. The process of claim 12 wherein the mycelia, which are subjected to extraction, are in the form of a wet cake.

14. The process of claim 13 wherein the extraction is carried out in two steps, the first step comprising: extracting the mycelia by comminuting it in the presence of a $C_2$-$C_4$ aliphatic alcohol and water; and separating the liquid medium containing the extracted lipids from the comminuted fungus bodies; and a second step which comprises mixing the comminuted fungus bodies separated in the first step with a $C_4$-$C_7$ aliphatic hydrocarbon solvent in the substantial absence of water to cause extraction of the residual fraction of lipids contained in the fungus bodies, and separating the hydrocarbon solvent containing extracted lipids from the fungus bodies.

15. The process of claim 14 wherein the amount of alcohol is in the range of about 2 to about 7 parts by weight per part by weight per dry weight of the fungal bodies, and the amount of water is from about 0.2 to about 0.7 parts by weight per weight of alcohol.

16. The process of claim 15 wherein the alcohol is selected from ethanol, propanol, and isopropanol, and the hydrocarbon solvent is selected from hexane and cyclohexane.

17. The method of claim 16 wherein the amount of hydrocarbon solvent is from about 2 to about 8 parts by weight per dry weight of the fungal bodies.

* * * * *